(12) United States Patent
Cui et al.

(10) Patent No.: US 7,827,852 B2
(45) Date of Patent: Nov. 9, 2010

(54) GAS SENSOR AND METHOD OF MAKING

(75) Inventors: Jun Cui, Glenville, NY (US); John Patrick Lemmon, Schoharie, NY (US); Kalaga Murali Krishna, Bangalore (IN); Geetha Karavoor, Kerala (IN); Vinayak Tilak, Niskayuna, NY (US); Mohandas Nayak, Karnataka (IN); Ravikumar Hanumantha, Karnataka (IN)

(73) Assignee: General Electric Company, Niskayuna, NY (US)

( * ) Notice: Subject to any disclaimer, the term of this patent is extended or adjusted under 35 U.S.C. 154(b) by 391 days.

(21) Appl. No.: 11/961,092

(22) Filed: Dec. 20, 2007

(65) Prior Publication Data

US 2009/0159446 A1 Jun. 25, 2009

(51) Int. Cl.
*G01N 7/10* (2006.01)
(52) U.S. Cl. .................................. 73/31.06
(58) Field of Classification Search ............. 73/32.31, 73/31.05, 31.06; 422/98
See application file for complete search history.

(56) References Cited

U.S. PATENT DOCUMENTS

| | | | | |
|---|---|---|---|---|
| 4,338,281 | A * | 7/1982 | Treitinger et al. | 422/98 |
| 4,569,826 | A * | 2/1986 | Shiratori et al. | 422/90 |
| 5,302,935 | A | 4/1994 | Chatterjee | |
| 5,546,004 | A | 8/1996 | Schmelz | |
| 5,627,305 | A | 5/1997 | Yun et al. | |
| 5,811,662 | A * | 9/1998 | Williams et al. | 73/31.06 |
| 6,012,327 | A * | 1/2000 | Seth et al. | 73/31.06 |
| 6,113,859 | A | 9/2000 | Kim et al. | |
| 6,774,613 | B1 | 8/2004 | Becker et al. | |
| 6,993,955 | B1 * | 2/2006 | King et al. | 73/31.06 |
| 7,017,389 | B2 * | 3/2006 | Gouma | 73/31.05 |
| 7,341,694 | B2 * | 3/2008 | Nishiyama et al. | 422/90 |
| 7,531,136 | B2 * | 5/2009 | Besnard et al. | 422/82.02 |
| 2002/0146352 | A1 | 10/2002 | Wang et al. | |
| 2004/0132202 | A1 | 7/2004 | Nishiyama et al. | |
| 2004/0213701 | A1 * | 10/2004 | Hattori et al. | 422/98 |
| 2004/0248282 | A1 | 12/2004 | Sobha et al. | |

(Continued)

FOREIGN PATENT DOCUMENTS

EP 0046989 8/1981

(Continued)

OTHER PUBLICATIONS

Lambert-Mauriat et al., "Density-functional study of oxygen vacancies in monoclinic tungsten oxide," J. Phys.: Condens. Matter 18 (2006); pp. 7361-7371.*

(Continued)

*Primary Examiner*—John Fitzgerald
(74) *Attorney, Agent, or Firm*—Joseph J. Christian

(57) ABSTRACT

A gas sensor is disclosed. The gas sensor includes a gas sensing layer including doped oxygen deficient tungsten oxide and a dopant selected from the group consisting of Re, Ni, Cr, V, W, and a combination thereof, at least one electrode positioned within a layer of titanium, and a response modification layer. The at least one electrode is in communication with the gas sensing layer and the gas sensing layer is capable of detecting at least one gas selected from the group consisting of NO, $NO_2$, $SO_x$ $O_2$, $H_2O$, and $NH_3$. A method of fabricating the gas sensor is also disclosed.

25 Claims, 8 Drawing Sheets

U.S. PATENT DOCUMENTS

| | | | |
|---|---|---|---|
| 2005/0072213 A1* | 4/2005 | Besnard et al. | 73/31.06 |
| 2005/0167592 A1 | 8/2005 | Moon et al. | |
| 2006/0091022 A1* | 5/2006 | Ruud et al. | 205/775 |
| 2006/0249384 A1 | 11/2006 | Kim et al. | |
| 2006/0277974 A1 | 12/2006 | Gouma et al. | |
| 2007/0281160 A1* | 12/2007 | Krishna et al. | 428/403 |
| 2008/0008625 A1* | 1/2008 | Thomas et al. | 422/82.05 |
| 2009/0159445 A1* | 6/2009 | Krishna et al. | 204/424 |
| 2009/0159447 A1* | 6/2009 | Cui et al. | 204/431 |

FOREIGN PATENT DOCUMENTS

| | | |
|---|---|---|
| EP | 46989 A2 * | 3/1982 |
| EP | 0940673 A2 | 9/1999 |
| EP | 0767905 B1 | 12/1999 |
| EP | 1112486 A1 | 2/2000 |
| EP | 1110081 B1 | 3/2003 |
| EP | 1403637 A1 | 3/2004 |
| EP | 1452855 A1 | 9/2004 |
| EP | 1560008 A1 | 8/2005 |
| EP | 1591776 A1 | 11/2005 |
| JP | 2001343347 A | 6/2000 |

OTHER PUBLICATIONS

Penza et al., "Tungsten trioxide (WO3) sputtered thin films for a NOx gas sensor," Sensor adn Actuators B 50 (1998), pp. 9-18.*

Stankova et al., "Improvement of the Gas Sensing Properties of rf Sputtered WO3 Thin Films Using Different Dopants", IEEE Explore, 2005, pp. 553-556.

Chung et al., "Gas Sensing Properties of WO3, Thick Film for NO2 Gas Dependent on Process Condition", Sensors and Actuators B 60 (1999) 49-56.

Ashraf et al., "The Gas-sensing Properties of WO3-x Thin Films Deposited Via the Atmospheric Pressure Chemical Vapour Deposition (APCVD) of WCl6 With Ethanol", Measurement Science and Technology, 19 (2008) (9 pages).

Jimenez et al., "Gas Sensing Properties of Catalytically Modified WO3 With Copper and Vanadium for NH3 Detection", IEEE Explore, 409-414.

* cited by examiner

GAS SENSOR AND METHOD OF MAKING

BACKGROUND

The invention relates generally to the area of gas sensing. More specifically, the invention relates to the sensing of $NO_x$ gas.

Environmental considerations are the primary motivating factors to develop $NO_x$ gas sensors. $NO_x$ emissions react with gases such as $SO_x$, CO and moisture (water vapor) in the air to produce smog and acid rain. One of the major sources of $NO_x$ emissions is automobile exhaust.

The European Euro VI emission standards for light commercial vehicles (category N1-I, N1-II and N1-III), to be implemented by September 2015, require $NO_x$ emission levels below 0.5 gm/hp-hr. This typically translates to less than 50 ppm of $NO_x$ tail pipe emissions. Development of cost-effective gas sensors that can give reliable readout at such low concentration levels of analyte, and which can deliver robust performance even in harsh environments, is one of the major challenges facing present day emissions monitoring technology.

The current paradigm in improving the efficiency of internal combustion engines utilizes the technology of lean burn, whereby very high air:fuel ratios (~$10^2$:1), as compared to conventional stoichiometric ratio (typically ~20:1), are used. While the lean burn technology improves the efficiency of the engine, it also results in higher $NO_x$ emissions.

Any emissions control scheme that adversely impacts or limits efficiency will not be commercially viable. This necessitates real time monitoring of $NO_x$ emission levels and use of this information to dynamically control engine operating parameters (such as compression ratio etc) and exhaust after-treatment systems (such as catalytic filters etc) to achieve enhanced engine efficiency and enhanced emissions control respectively.

One of the current $NO_x$ gas sensing technologies in the market employs yttria stabilized zirconia (YSZ) based gas sensors. The gas sensors are essentially a multi-chamber electrochemical cell measuring the oxygen changes as a result of $NO_x$ decomposition. Such technology requires catalysts such as Pt. However, the performance of the catalyst degrades upon exposure to $SO_x$ and water vapor, as are commonly present in the exhaust from automobiles. This is one of the factors contributing to lowering the working life of such gas sensors. Further, the relatively intricate design of these gas sensors makes them expensive to replace on a regular basis.

Another current gas sensing technology in the market employs semiconductor gas sensors. As with any technology, this technology presents situation specific disadvantages and advantages. For example, gas emissions monitoring applications often require quantitative estimation of a particular or few gas species (e.g., $NO_x$) in a multiple gas species environment. These gas sensors however, are sensitive to a broad range of gases, and therefore are of limited utility in such applications. Furthermore, these gas sensors are prone to long term instability because of their polycrystalline nature. On the other hand, this technology has the advantages of being solid-state, such as rigid construction and compact size. Further, the technology is amenable to readout using simple electronics thereby reducing cost of system manufacture, operation, maintenance and replacement. In addition, semiconductor gas sensors admit wide range of response tunability via introduction of suitable dopants, control of morphology of gas sensing surface, control of gas sensor operating parameters, amongst other controllable factors.

A gas sensor that is semiconductor based, can make quantitative estimation of $NO_x$ gas even at low concentration levels, and have a long working life, would therefore, be highly desirable.

BRIEF DESCRIPTION

Embodiments of the invention are directed towards a gas sensor and a method for making the gas sensor.

In accordance with one exemplary embodiment of the invention, a gas sensor is provided. The gas sensor includes a gas sensing layer including $WO_{3-\delta}$, wherein $0.35 \geq \delta > 0$ and including a dopant selected from the group consisting of Re, Ni, Cr, V, W and a combination thereof. At least one electrode is positioned within a layer of titanium and a response modification layer of a material selected from the group consisting of Ti, Ni, Cr, V, W, Re, and a combination thereof, the at least one electrode being in communication with the gas sensing layer, wherein the gas sensing layer is capable of detecting at least one gas selected from the group consisting of NO, $NO_2$, $SO_x$, $O_2$, $H_2O$, and $NH_3$.

In accordance with another exemplary embodiment of the invention, an automobile including a system for gas sensing is provided. The automobile includes an exhaust system to transport gases, and a gas sensor. The gas sensor includes a gas sensing layer including $WO_{3-\delta}$, wherein $0.35 \geq \delta > 0$ and including a dopant selected from the group consisting of Re, Ni, Cr, V, W, and a combination thereof. At least one electrode is positioned adjacent to a layer of titanium and a response modification layer of a material selected from the group consisting of Ti, Ni, Cr, V, W, Re, and a combination thereof, the at least one electrode being in communication with the gas sensing layer, wherein the gas sensing layer is capable of detecting at least one gas selected from the group consisting of NO, $NO_2$, $SO_x$, $O_2$, $H_2O$ and $NH_3$.

In accordance with another exemplary embodiment of the invention, a method for making a gas sensor is provided. The method includes providing a substrate, disposing a heating layer adjacent to the substrate layer, disposing a first glass layer adjacent to the heating layer, disposing a temperature sensing layer adjacent to the first glass layer, disposing a second glass layer adjacent to the temperature sensing layer, disposing at least one electrode adjacent to the second glass layer, disposing a titanium layer adjacent to the at least one electrode, disposing a response modification layer adjacent to the titanium layer, and disposing a gas sensing layer comprising $WO_{3-\delta}$, wherein $0.35 \geq \delta > 0$, and comprising a dopant selected from the group consisting of Re, Ni, Cr, V, W and a combination thereof, adjacent to the titanium layer.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
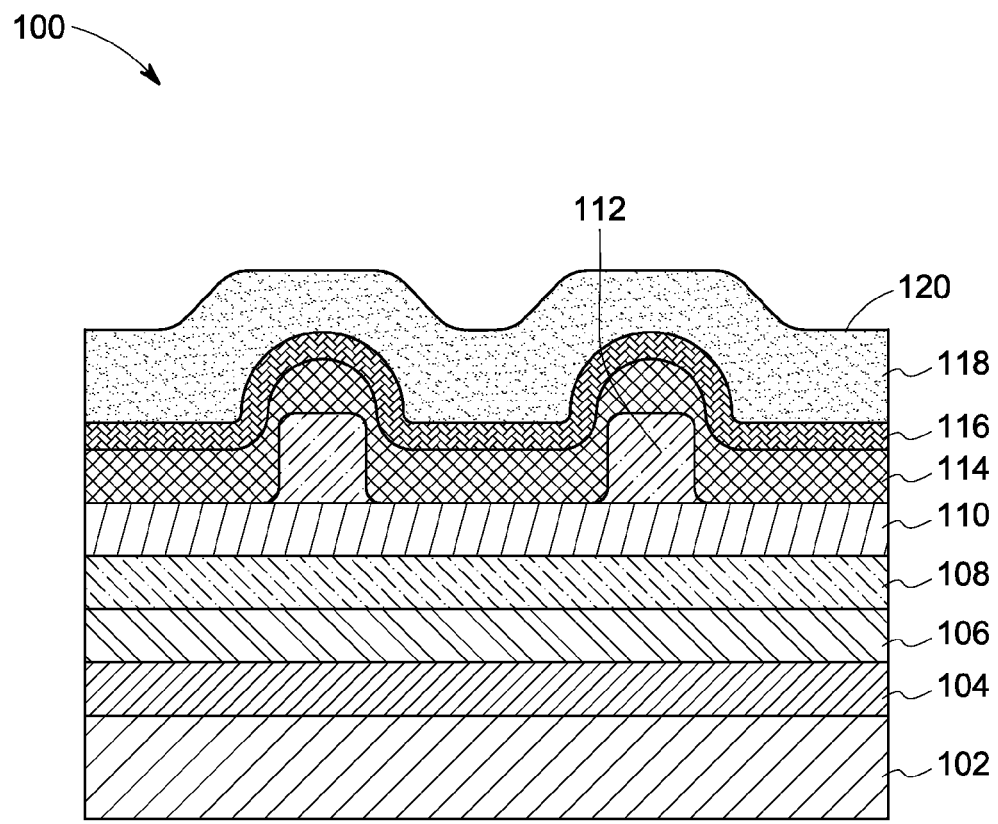
FIG. 1 is a diagrammatical representation of a cross-sectional view of a $NO_x$ gas sensor in accordance with an exemplary embodiment of the invention.

In the following description, whenever a particular aspect or feature of the invention is said to comprise or consist of at least one element of a group and combinations thereof, it is understood that the aspect or feature may comprise or consist of any of the elements of the group, either individually or in combination with any of the other elements of that group.

A gas sensor may be used to determine if an "analyte" is present and/or to quantify an amount of the analyte. As used herein, the term "analyte" may refer to any substance to be detected and/or quantified, including but not limited to a gas, a vapor, a bioanalyte, particulate matter, and a combination thereof.

Since the primary constituents of $NO_x$, i.e., NO and $NO_2$ are interconvertible, reliable estimation of total $NO_x$ may be achieved if the response of the gas sensor, i.e., the $NO_x$ concentration dependent change in resistance of the gas sensor is equal (in terms of magnitude and sign) for both NO and $NO_2$. Thus, if $\Delta R(NO_2, c)$ and $\Delta R(NO, c)$ be the response of the senor to concentration "c" of $NO_2$ and NO respectively, then a response ratio "rr" (defined below) close to unity would be desirable.

$$rr = \Delta R(NO_2, c)/\Delta R(NO, c) \quad (1)$$

As used herein, the term "equisensitivity" refers to "rr" defined according to equation (1) when it is in a range from about 0.5 to about 3.

As used herein, the term "adjacent," when used in context of discussion of different components comprising the gas sensor refers to "immediately next to" or it refers to the situation wherein other components present between the components under discussion.

As used herein, the term "communication," when used in context of discussion of more than one component comprising the gas sensor may mean that any change in an electrical characteristic of one component is reflected at, and therefore, detectable and measurable via, the other component.

As used herein, the term "harsh environment" or "harsh environments" refers to an environment within a volume that is in the vicinity of the gas sensing layer, and in which are present the analytes whose detection and/or estimation is being sought. The temperature within this volume may not be uniform, i.e., the temperature at/of different locations within this volume can be different, and can be from about 200° C. to about 800° C. At different locations within this volume can also be present different amounts of corrosive chemical species including but not limited to $NO_x$, $SO_x$, $H_2O$, particulate matter, hydrocarbons, and a combination thereof.

As used herein, the term "response modification layer" refers to a layer which serves to introduce dopants into a gas sensing layer via surface doping through the mechanism of diffusion. This surface doping may result in a modification of the response of the gas sensing layer for a given set of operating parameters and/or operating environments.

As used herein, the term "glass" refers to any suitable material that may be used to form a separating layer, that in a given embodiment of the gas sensor, has sufficient thermal conductivity to provide a sufficiently large heat link between the elements that the separating layer segregates, and which has sufficient electrical resistivity to provide sufficient electrical resistance between the elements that the separating layer segregates.

If the response of a particular embodiment of the gas sensor changes as a result of introduction or withdrawal of the analyte, then as used herein in context of the time of response of the particular embodiment of the gas sensor, the term "fast", "slow", and "medium" should be understood as follows: let the gas sensor be exposed to a given analyte for a duration "$t_{on}$" of time, subsequent to which let the analyte be withdrawn for a duration "$t_{off}$" of time. Let the response of the particular embodiment of the gas sensor at the end of "$t_{on}$" and "$t_{off}$" be "$rf_{on}$" and "$rf_{off}$" respectively. Then the term "fast response time" refers typically to the situation where the particular embodiment of the gas sensor achieves at least 0.9 times rf within the first minute of exposure to the analyte, i.e., the response of the embodiment of the gas sensor tends to "plateau" off after the first minute of exposure to the analyte. Another way of saying this is that an anomalous change in time derivative of the response versus time profile occurs within the first minute or thereabouts of exposure to analyte. In similar vein, if the response of the gas sensor does not exhibit a plateau for the entire duration of exposure to analyte then we the term "slow response time" is used to characterize the time response. The term "medium response time" is used to characterize the time response when the response of the gas sensor can be characterized as neither "fast" nor "slow", typically, when the gas sensor achieves, within the first minute of exposure to analyte, a response of less than 0.5 times rf. If the response of the particular embodiment of the gas sensor changes as a result of withdrawal of the analyte, then as used herein in context of the time of recovery of the particular embodiment of the gas sensor, the term "fast recovery time" refers typically to the situation where the particular embodiment of the gas sensor withdraws at least 0.9 times rf within about two to three minutes of withdrawal of the analyte. Another way of saying this is that an anomalous change in time derivative of the response versus time profile occurs within the two or three minutes or thereabouts of withdrawal of analyte. In similar vein, if the response of the gas sensor does not exhibit any such anomalous change in the previously mentioned time derivative up to the entire duration of twenty minutes, then the term "slow recovery time" is used to characterize the recovery time. The term "medium recovery time" is used to characterize the recovery times when the recovery of the gas sensor can be characterized as neither "fast" nor "slow", typically, when it takes the gas sensor response about ten to about fifteen minutes to come to within 0.9 times rf.

A gas sensor can be any device capable of producing an electrical signal proportional to an electrical characteristic that can be modulated upon exposure to gases. Examples of suitable devices include, but are not limited to, a resistor, a field effect transistor, a capacitor, a diode, and a combination thereof.

Examples of suitable gases to be sensed include, but not limited to, NO, $NO_2$, $SO_x$, $O_2$, $H_2O$ and $NH_3$ and combinations thereof. In one embodiment, the gas sensor is not susceptible to poisoning by $SO_2$ and $CO_2$ gases.

Referring to the drawings in general and to FIG. 1 in particular, it will be understood that the illustrations are for the purpose of describing a preferred embodiment of the invention and are not intended to limit the invention thereto.

FIG. 1 is a diagrammatical representation of one embodiment of a gas sensor 100 that may be used to detect an analyte in accordance with an exemplary embodiment of the invention. Although, $NO_x$ is used as an example with respect to some of the embodiments described herein, note that the gas sensor may be useful to detect other analytes, such as, for example, $SO_x$, $NH_3$. The gas sensor 100 might be, for example, an in-situ gas sensor that directly samples a gas stream to be analyzed. In this way, the sensor 100 can be exposed to the gas stream and generate a detection signal indicating whether a particular analyte (e.g., $NO_x$) is present. The gas sensor 100 can also generate a signal proportional to the concentration of the analyte and thereby measure the concentration of the analyte.

The illustrated embodiment 100 includes a substrate 102. On this substrate layer is disposed a heater 104. A first glass layer 106 is positioned above the heater. On the first glass layer 106 is disposed a temperature sensing layer 108. A second glass layer 110 is positioned above the temperature sensing layer. On the second glass layer 110 is disposed at least one electrode 112. A titanium layer 114 that completely covers the at least one electrode, and which is also in contact with the second glass layer 110 upon which is disposed at least one electrode. A response modification layer 116 is disposed on to the titanium layer. Upon this response modification layer is disposed a gas sensing layer 118 which has a gas sensing surface 120. In some embodiments, the gas sensor may include an element for heating the gas sensor. In one embodiment, an element for heating the gas sensor may be disposed adjacent to the gas sensing layer or, adjacent to the substrate layer, or on the packaging and any combinations thereof, and/or be covered with an electrically insulating and thermally conducting layer. The heating means may be an element that is separate from the main gas sensor, such as a metal (e.g., Pt) layer disposed adjacent to the gas sensing layer. In the embodiment illustrated in FIG. 1, the element 104 is a 25 Ω(Ohm) Pt heater that may be used to heat the gas sensor to a desired temperature. The heating means may also be the gas sensing layer itself. In one non-limiting example, a large current may be passed through the gas sensing layer in order to heat it to a desired temperature. The addition of heat, to the surface of the gas sensing layer may also result in faster response and recovery times. Not to be limited by any particular theory, it is believed that the heat decreases the resident time of each gas species at the surface of the gas sensing layer. The heating means may also allow for adjusting the temperature of the gas sensor to allow for higher sensitivity to gas species that are predisposed to superior detection at higher temperature ranges even when the gas stream environment to be measured has not reached such temperatures. This may be important in such applications that require sensing when an engine has only recently been started. Keeping the gas sensor at a constant temperature, such as the maximum operable temperature, can also be used to ignore any dependence of the response signal on temperature, thus, allowing for simpler interpretation of the response signal. Additionally, the heating of the gas sensor may be intentionally modified to provide a selective response to a variety of gases as driven by the gas sensing layer temperature dependent selectivity and/or sensitivity to that species of gas. Selectivity as used herein, refers to the ability of a gas sensor to discriminate between different presented analyte species. Sensitivity as used herein, refers to the ability of a gas sensor to display a change in an electrical characteristic when an analyte is presented to it. Selectivity, therefore, may be due to differing sensitivities towards different analyte species.

In one embodiment, the substrate 102 shown in FIG. 1 may be composed of Alumina. In another embodiment, the substrate 102 shown in FIG. 1 may be composed of yttria stabilized zirconia. In yet another embodiment, the substrate 102 shown in FIG. 1 may be composed of zirconia.

The glass layers 106 and 110 as shown in FIG. 1, are layers of thermally conducting but electrically insulating materials that are interposed between the heater 104 and temperature sensing layer 108, and between the temperature sensing layer 108 on one side and the at least one of the electrode 112 and titanium layer 114 on the other side, respectively. Such glass layers 106 and 110, composed of such thermally conducting but electrically insulating materials, allow heat to be transported across the gas sensor, yet inhibit electrical contact between the heater and the temperature sensing layer or, and between the temperature sensing layer 108 on one side and the at least one of the electrodes 112 and titanium layer 114 on the other side, respectively. Examples of suitable materials for glass layers include, but are not limited to, polysilicate glass, silicon dioxide, silicon nitride, and any combinations thereof. The glass layer 110 may also be subjected to physical and chemical treatments to enable enhanced physical adhesion of the at least one electrode and titanium layer to itself. Further, varying thicknesses of glass layers should allow for different amounts of heat links and electrical resistances between their respective enclosing layers.

In one embodiment, the oxygen deficiency (δ) in the host metal oxide $WO_{3-\delta}$ can be from about 0 to about 0.5. In another embodiment, the oxygen deficiency (δ) in the host metal oxide $WO_{3-\delta}$ can be from about 0 to about 0.35.

In one embodiment, the dopant in the gas sensing layer 118 may be selected from the group consisting of Re, Ni, Cr, V, W, and a combination thereof. In another embodiment, the dopant in the gas sensing layer 118 can be selected from the group consisting of Re, V and a combination thereof.

In one embodiment, the oxidation state of the dopant may be such that the dopant is of n type, e.g., when the dopant is Re in a suitable oxidation state. In another embodiment, the oxidation state of the dopant may be such that the dopant is of p type, e.g., when the dopant is V in a suitable oxidation state. In yet another embodiment, the oxidation state of the dopant may equal the oxidation state of the metal (W) in the metal oxide that the gas sensing layer is composed of, so that the dopant is neither n type nor p type.

In one example, the response to a given concentration of at least one analyte may be enhanced by varying the thickness of the gas sensing layer. In one embodiment, the gas sensing layer 118 can have a thickness from about 300 Å to about 5000 Å. In another embodiment, the gas sensing layer 118 can have a thickness from about 500 Å to about 1500 Å. In yet another embodiment, the gas sensing layer 118 can have a thickness from about 700 Å to about 1200 Å.

A response modification layer 116 is interposed between the gas sensing layer and the titanium layer. This response modification layer is composed of a material selected from the group consisting of Ti, Ni, Cr, V, W, Re and a combination thereof. In one embodiment, the response modification layer 116 can have a thickness from about 10 Å to about 100 Å. In another embodiment, the response modification layer 116 can have a thickness from about 20 Å to about 80 Å. In yet another embodiment, the response modification layer 116 can have a thickness from about 30 Å to about 60 Å. In one embodiment of the gas sensor, the response modification layer may aid the gas sensor in having an equisensitive response to any two given gases. In another embodiment of the gas sensor, the response modification layer may aid the gas sensor in having a desired value of baseline resistance. In yet another embodiment of the gas sensor, the response modification layer may aid the gas sensor in having desired levels of response and recovery times upon exposure to and withdrawal of analyte respectively. Not to be limited by any particular theory, it is possible that the response modification layer helps improve the working characteristics of the gas sensor by inhibiting direct physical contact between the gas sensing layer and the titanium layer.

In one embodiment, the response modification layer may be composed of a mixture of Ti with at least one chemical element selected from the group consisting of Ni, Cr, V, W, and Re.

The titanium layer 114 serves as an adhesion layer to anchor the response modification layer upon which is disposed the gas sensing layer. In one embodiment, the titanium layer 114 can have a thickness from about 5 Å to about 100 Å. In another embodiment, the titanium layer 114 can have a thickness from about 10 Å to about 50 Å. In yet another embodiment, the titanium layer 114 can have a thickness from about 15 Å to about 30 Å.

At least one of the electrodes 112 may be made from any material capable of physical adhesion and electrical contact to its adjacent layers. Examples of suitable materials for the at least one electrode include, but are not limited to, Pt, Au, Ag, Ni, Ti, In, Sn, Cr, nickel nitride, titanium nitride, aluminum doped zinc oxide (ZAO), indium tin oxide (ITO), chrome, and any combination thereof.

In one embodiment, the electrodes 112 can have a thickness from about 500 Å to about 10000 Å. In another embodiment, the electrodes 112 can have a thickness from about 800 Å to about 3000 Å.

In one embodiment, at least one of the at least one electrode 112 may be a multilayer stack of materials. Examples of suitable materials to comprise the different layers of the multilayer stack include, but are not limited to, Pt, Ti, Al, Au, Ag, Ni, In, Cr, nickel oxide, titanium nitride, aluminum doped zinc oxide, indium tin oxide, chrome, and any combination thereof.

In one embodiment in which at least one of the at least one electrode 112 is a multilayer stack of materials, the thickness of each layer can be from about 100 Å to about 2000 Å. In another embodiment, in which the electrodes are a multilayer stack of materials, the thickness of each layer can be from about 300 Å to about 1500 Å. In yet another embodiment, in which the electrodes are a multilayer stack of materials, the thickness of each layer can be from about 500 Å to about 1000 Å.

Figure 2:
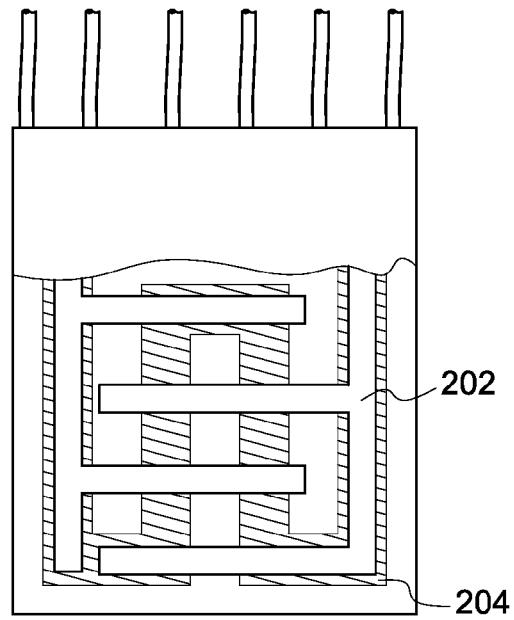
FIG. 2 is a diagrammatical representation of the top view of interdigitated sensing electrodes in a $NO_x$ gas sensor, in accordance with an exemplary embodiment of the invention.
Figure 3:
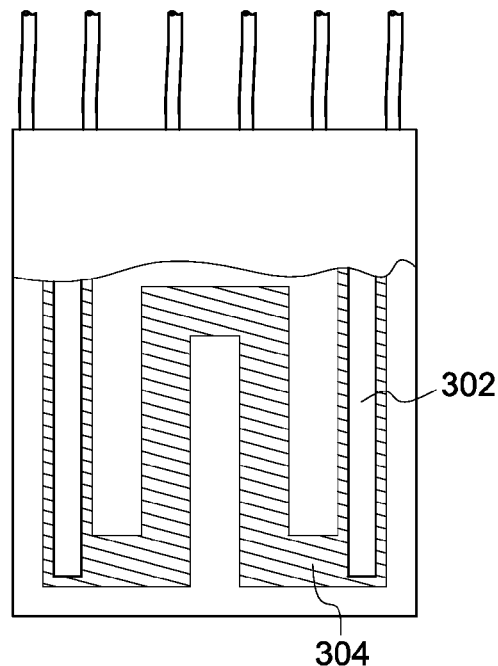
FIG. 3 is a diagrammatical representation of the top view of inline sensing electrodes in a $NO_x$ gas sensor, in accordance with another exemplary embodiment of the invention.

In one embodiment, the electrodes 112 can be placed in an interdigitated geometry 202 as shown in the embodiment 200 in FIG. 2. Element 204 of FIG. 2 shows the geometry of underlying heater layer 104. In another embodiment, the electrodes 112 can be placed in an inline geometry 302 as illustrated in the embodiment 300 in FIG. 3. Element 304 of FIG. 3 shows the geometry of underlying heater layer 104.

In one embodiment, the at least one electrode may be placed adjacent to the gas sensing layer in a "sandwich" geometry, i.e., at least one electrode is disposed on either side of the gas sensing layer along its thickness direction. In another embodiment, the at least one electrode may be placed in a "side-by-side" geometry, i.e., at least two electrodes are disposed adjacent each other on the same side of the gas sensing layer. In another embodiment, a titanium layer may be placed along those surfaces of the at least one electrode that are closest to adjacent components of the gas sensor.

In one embodiment, the gas sensing layer 118 can have a dopant concentration from about 0.2 mol % to about 5 mol %. In another embodiment, the gas sensing layer 118 can have a dopant concentration from about 0.5 mol % to about 4 mol %. In yet another embodiment, the gas sensing layer 118 can have a dopant concentration from about 2 mol % to about 3 mol %.

In some embodiments, the gas sensor may include a way of measuring the temperature of the device. A means of measuring the temperature may be disposed anywhere within the gas sensor. For example, it may be disposed adjacent to the gas sensing layer or, adjacent to the substrate layer, or on the packaging, or any combination thereof, and/or be covered with an electrically insulating and thermally conducting layer. The temperature sensing means may include but not limited to, a resistive temperature device, a thermocouple, a silicon bandgap temperature sensor and a combination thereof. The temperature sensing means may be a separate element, such as a metal (e.g., Pt) layer disposed adjacent to the gas sensing layer.

The temperature sensor can be of various types, including but not limited to, a thermocouple, a resistance temperature detector, a silicon bandgap temperature sensor, or a thermistor. The thermocouple temperature sensor can be of various types, including but not limited to Type K (CHROMEL®/ALUMEL®), Type J (Iron/Constantan), Type N (NICROSIL®), Type B, Type R, Type S, Type T (Copper/Constantan), Type C. The resistance temperature detector can be composed of various metals, but are usually made from Pt. The silicon bandgap temperature sensor can be composed of pure silicon or of chemical compounds of silicon including but not limited to silicon carbide. The thermistor temperature sensor can be composed of various materials including but not limited to ceramics and polymers. These materials can have a positive or a negative temperature coefficient of resistance. The temperature sensors may be biased in various ways, including but not limited to, voltage biasing and current biasing. Furthermore, the response of the temperature sensors may be recorded by means including but not limited to resistive measurement, potentiometric measurement and a combination thereof. The temperature sensor layer 108 shown in FIG. 1 is a thermocouple.

Other gas sensor operating and geometry parameters being fixed, the response to a given concentration of any particular analyte may be enhanced when the gas sensing layer is maintained at particular temperatures. In certain embodiments, enhanced sensitivity may be achieved by maintaining the temperature within the range from about 300° C. to about 550° C.

Conceivably, different applied direct current (DC), alternating current (AC), or a combination thereof, of bias levels to the gas sensing layer may enhance the gas sensing characteristics such as selectivity and sensitivity towards one or another analyte. For example, according to some embodiments, varying levels of a DC bias may be used to adjust the sensitivity of the gas sensor 100 to different gas species in an analyte. For example, a gas sensor operating under a given first DC bias level might be preferentially sensitive to a first analyte species, a gas sensor operating under a second DC bias level might be preferentially sensitive to a second analyte species, and so on for different DC bias levels. This property may be used to selectively detect and measure different species of analyte. The AC and/or DC bias used in the operation of the gas sensor may be an electrical current, an electrical voltage or a combination thereof. The AC or DC response of the gas sensor during operation of the gas sensor may be an electrical current, an electrical voltage or a combination thereof.

The gas sensor may also be configured so as to have suitable one or more filters that allow only specific analytes to pass through and impinge onto, i.e., make contact, with the gas sensing layer. Conceivably, such filters may aid selective detection of given one or more analytes. Such filters may also aid in limiting the passage of certain analytes such as, for instance, particulate matter, towards the gas sensing layer. In some embodiments, membranes that serve as filters towards particular chemical or physical species present in the environment of the gas sensor may be disposed adjacent to the gas sensing layer. Such filters would provide a means for limiting or regulating the type and/or the amount of gas or particulate species that contact the gas sensing layer of the gas sensor. Examples of suitable means for limiting or regulating the type and/or amount of gas species include, but are not limited to, a thin film, such as of Kapton, or Teflon, porous membrane filter medium (e.g., steel wool or quartz wool), an about 10 Å thick film of Pd, porous ceramic materials such as $Al_2O_3$, YSZ, $SiO_2$, and any combinations thereof. Conceivably, more than one gas sensor may be placed adjacent to each other or at different locations within the environment. Each of these gas sensors may share with each other the same filter, or may individually have one or more, same or different filters. Such an "array" of gas sensors may be used to selectively detect and/or measure the concentrations of different analyte species at different locations within the environment.

Figure 4:
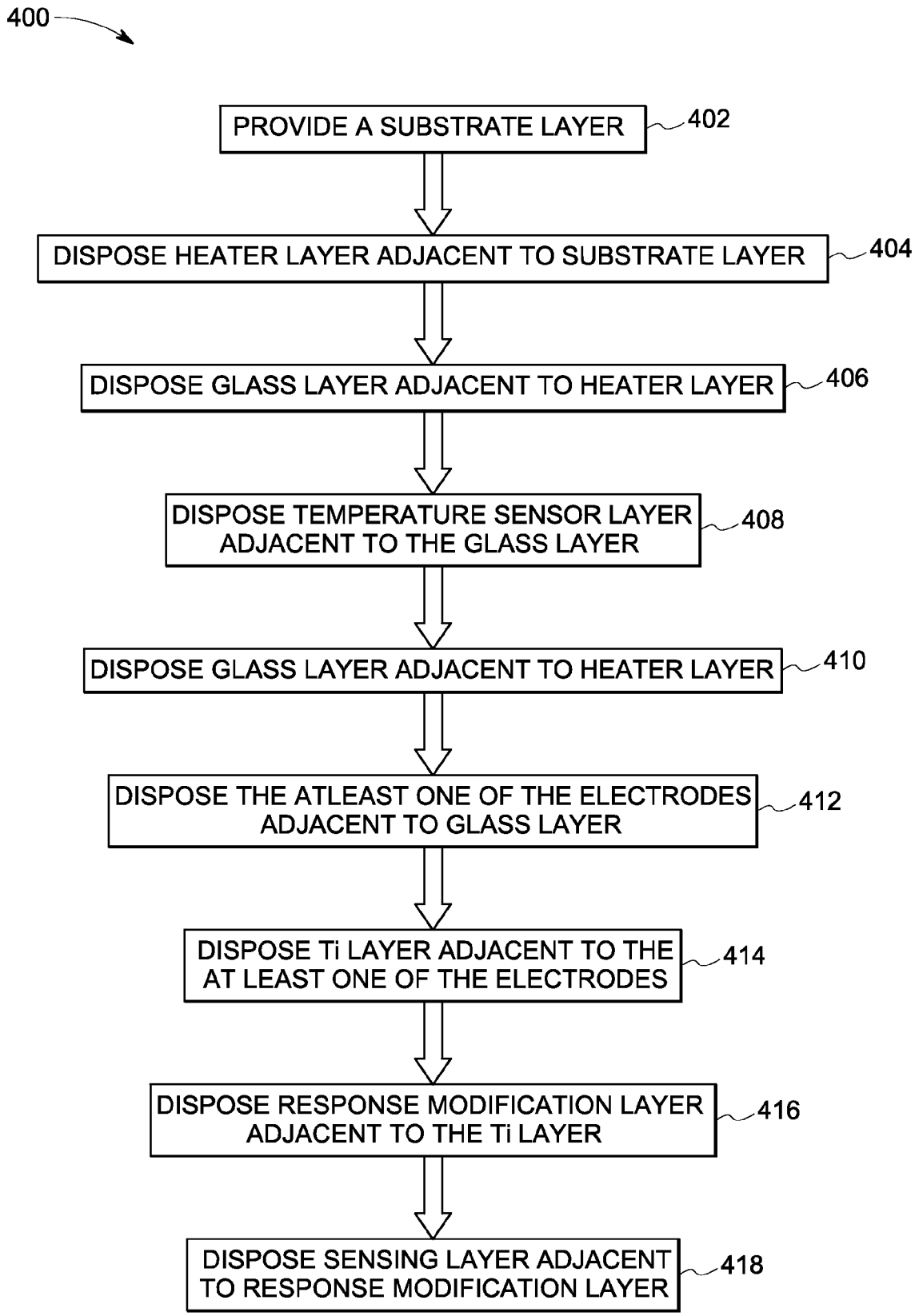
FIG. 4 is a flow chart representation of a manufacturing process of a $NO_x$ gas sensor in accordance with an exemplary embodiment of the invention.

FIG. 4 is a flow chart illustrating a method 400 for manufacturing the gas sensor in accordance with an exemplary embodiment of the invention. At step 402, a substrate layer is provided. At step 404, a heater layer is disposed adjacent to the substrate layer. At step 406, a glass layer is disposed adjacent to the heater layer, followed by step 408, where a temperature sensing layer is disposed adjacent to the glass layer. At step 410, a glass layer is disposed adjacent to the temperature sensing layer. At step 412, at least one electrode is disposed adjacent to the insulating layer. At step 414, a titanium layer is disposed adjacent to the at least one electrode. At step 416 a response modification layer is disposed adjacent to the titanium layer. At step 418, a gas sensing layer is disposed adjacent to the response modification layer.

Figure 5:
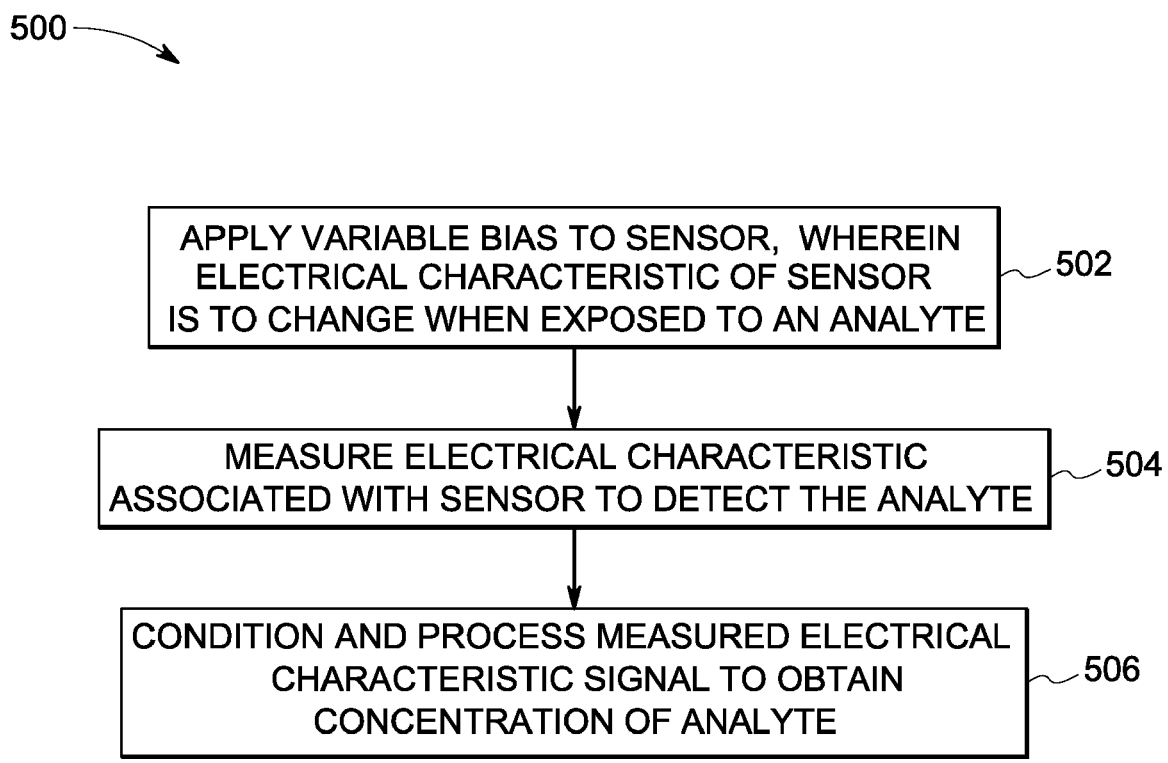
FIG. 5 is a flow chart representation of a method for detecting the analyte in accordance with one exemplary embodiment of the invention.

FIG. 5 illustrates a method for detecting an analyte according to an embodiment of the invention. At step 502, an analyte is allowed to impinge upon the gas sensing layer of the gas sensor causing a change in an electrical characteristic of the gas sensor. In step 504, the change in the electrical characteristic, which is being monitored continuously, is detected. If the functional relationship between the change in the electrical characteristic and the concentration of the applied analyte is known, then one may determine the concentration of the applied analyte from the measured change in the electrical characteristic, as is shown in step 506. Examples of suitable electrical characteristics include, but a are not limited to, electrical resistance, electrical capacitance, electrical current, electrical voltage, and a combination thereof. As an example, if the gas sensor is used under voltage bias conditions, the electrical characteristic might be, for instance, electrical current. Furthermore, such response signals might be monitored continuously to determine information about time evolution of concentration of an analyte.

In one embodiment, the response of the gas sensor, or of the material composing a sensing layer of the gas sensor, may be monitored via resistive measurement, potentiometric measurement, or combinations thereof.

In one embodiment, the response of the gas sensor may be tuned to be equisensitive to NO and $NO_2$ which are the two primary constituents of $NO_1$ emissions. The response ratio of the gas sensor for different concentrations of $NO_x$ may depend upon a plurality of system parameters and environment parameters, including but not limited to, the level of oxygen deficiency in the tungsten oxide film, the one or more dopants that are doped in the tungsten oxide film, the level of doping of the dopant, the microstructure/morphology of the of the gas sensing layer, the level of crystallinity of the gas sensing layer, the level of strain present in the gas sensing layer, the level of strain present in the titanium layer, the level of strain present in the response modification layer, the temperature at which the gas sensing layer is maintained while performing the gas sensing, the type and nature of the bias applied across the gas sensing layer, the presence or absence of the response modification layer, the level of adhesion of the gas sensing layer to the electrodes and to the underlying glass, the material, size, design, and placement of the electrodes. The microstructure/morphology of the gas sensing layer film may depend on the method used to grow the film. Some of the above mentioned system parameters are likely inter-related. In another embodiment, the response ratio of the gas sensor may depend upon the specific set of gas species that are present in the environment and on the individual concentrations of the different species present. For example, the presence of $H_2O$ in the environment being sensed may result in a modification in the response ratio of the gas sensor.

In one embodiment, the one or more dopants that are incorporated into the gas sensing layer may aid in modifying one or more response characteristics, including but not limited to, baseline resistance, response time, recovery time, of the gas sensor.

Figure 6:
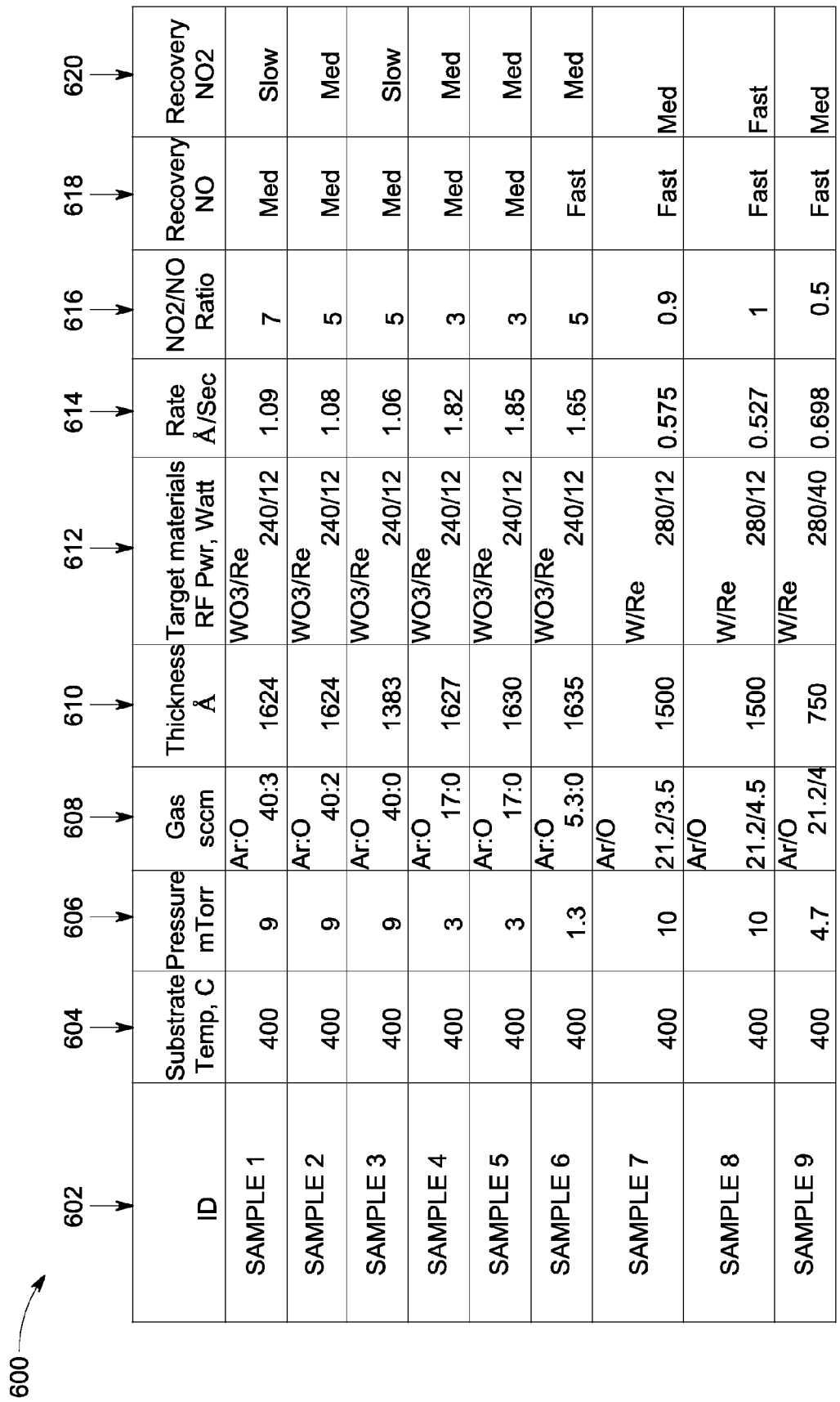
FIG. 6 is a table detailing the effect of oxygen deficiency state (δ) of a Re doped tungsten oxide film that constitutes the gas sensing layer, when the analyte is $NO_x$.

The oxygen deficiency state of the gas sensing layer may be one of the parameters affecting the response of the gas sensing layer. FIG. 6 is a table 600 of the effect of oxygen deficiency state ($\delta$) of a Re doped host tungsten oxide film that constitutes the gas sensing layer, when the analyte is $NO_x$. All the data presented in table 600 were obtained on gas sensing layers that were formed by the technique of reactive sputtering. The temperature 604 of all the gas sensors was maintained at 400° C. The oxygen deficiency state of the host film is an important parameter that can tune the response ratio of the gas sensor. The oxygen deficiency state of the gas sensing layer is dependent upon several factors related to the growth conditions of the gas sensing layer. These factors include, but are not limited to, the pressure of the sputtering gas in the reactive chamber 606, the exact composition of the sputtering gas, i.e., the ratio Ar:O 608, the thickness of the gas sensing layer 610, the composition of the targets used 612, and the rate at which the gas sensing layer was deposited 614. The performance of the gas sensors 602 may be quantified in terms of the response ratio 616, the time of recovery when the analyte is NO 618, and the time of recovery when the analyte is $NO_2$ 620. Samples 1 through 7 were grown by co-sputtering targets composed of $WO_3$ and Re. The use of a $WO_3$ target presents a certain minimum amount of oxygen at the location of deposition. For example, we see from table 600 that, for samples 1 through 3, at fixed substrate temperature 604 and pressure 606, and upon varying the Ar:O ratio 608 from 40:3 to 40:0, the response ratios 616 are nearly the same, and are substantially less than unity. The recovery times for these samples towards NO 618 and $NO_2$ 620 are also not substantially sensitive to the Ar:O ratio. A substantial reduction in sputtering gas pressure, as well as in the Ar:O concentration, with the expected concomitant reduction in the oxygen being presented to the being-deposited gas sensing layer, as for samples 4 through 6, also does not result in any substantial change in the response characteristics 616, 618, 620 from those obtained for the earlier samples 1 through 3. Using now, a W target instead of the earlier $WO_3$ target, with the concomitant decrease in the amount of oxygen being presented to the being-deposited gas sensing layer, as in for samples 7 through 9, results in substantially modified response characteristics 616, 618, 620. The table 600 therefore demonstrates the oxygen deficiency state of the gas sensing layer (which has a bearing on the response characteristics of the gas sensing layer) can be tuned by adjusting the oxygen level during the deposition of the gas sensing layer.

In the following measurements presented, the components of the gas sensor used may be grouped into two distinct sets depending on their source of origin and/or procurement. The five layers, i.e., the substrate 102, the heater 104 the first glass layer 106, the temperature sensing layer 108, and the second glass layer 110 were sourced from a commercial vendor. All other elements, i.e., the electrodes 112, the titanium layer 114, the response modification layer 116, and the gas sensing layer 118, were designed and implemented by the inventors.

The following results of measurements of the response of certain embodiments of the gas sensor were performed according to the following protocol: A mixture comprised of gases $N_2$, $O_2$, NO, $NO_2$, $SO_2$, $CO_2$, was first prepared by mixing the previously mentioned gases at 300° C. This mixture gas is then introduced into the chamber where the gas sensor is mounted. The response of the gas sensor, which is maintained at a temperature of about 400° C., is continuously monitored. The exact composition of the mixture gas is dependent upon the experiment being performed. For example, if the response time of the gas sensor to, say, 50 ppm (parts per million) of NO gas has to be ascertained, the mixture gas composition is 1000 sccm of $N_2$, 100 sccm of $O_2$, and 50 sccm of 1% NO balanced with $N_2$. This NO flow is maintained typically, for duration 8 or 10 minutes. The response time is obtained from the time evolution of the response upon the introduction of the NO gas in to the sample chamber. The recovery time is determined in similar vein by switching off of the flow of the NO gas, all other conditions remaining identical. The flow of NO is withdrawn, typically for duration 20 or 30 minutes. The recovery time is obtained from the time evolution of the response upon the withdrawal of the NO gas in to the sample chamber. This sequence of steps may be repeated to determine the reproducibility of the response.

In one embodiment, the gas sensing layer of the gas sensor may need to be conditioned before it displays desired and/or adequate response to any given one (or more) analyte(s). For example, when the method of deposition of the gas sensing layer is sputtering, then the as-deposited gas sensing layer is likely amorphous. This as-deposited gas sensing layer may not display desired or adequate response characteristics to, say, $NO_x$. Not to be limited by any particular theory, it is believed that changing the morphology of the gas sensing layer so as to tune its level of crystallinity, and/or grain size, and/or grain boundary interconnectivity, amongst other factors, will result in improved response characteristics of the gas sensor. It was determined that annealing the gas sensing layer at high temperatures in the presence of gases which contain nitrogen and oxygen (e.g., $NO_x$) resulted in the development, in the gas sensing layer, of desired response characteristics towards $NO_x$.

Figure 7:
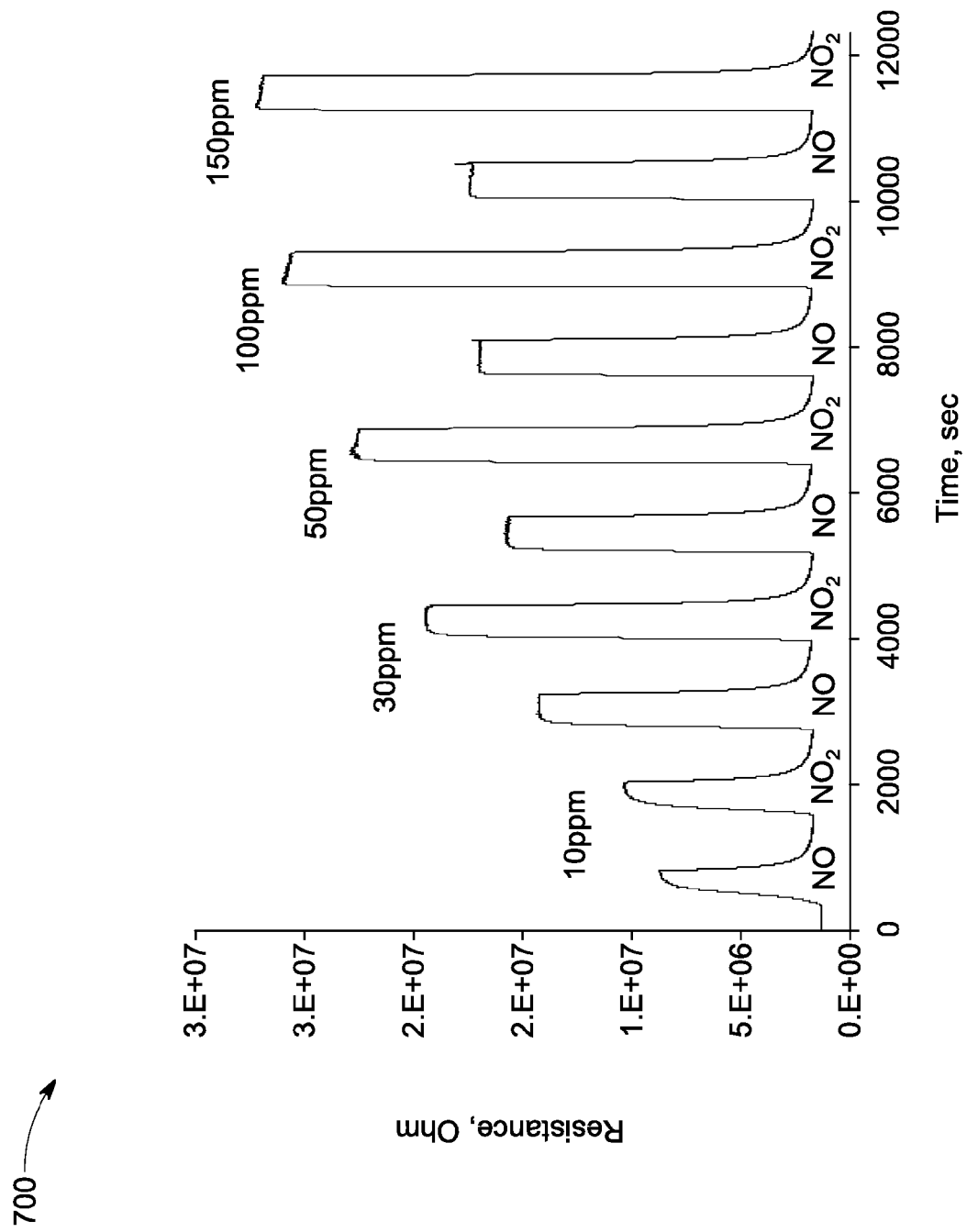
FIG. 7 is a graphical representation of the variation in gas sensor response upon exposure to different indicated NO and $NO_2$ gas levels, wherein the dopant species in a gas sensing layer of the gas sensor is Re, in accordance with one exemplary embodiment of the invention.

FIG. 7 is a graph 700 illustrating the resistance response of the gas sensor over time according to an exemplary embodiment of the invention when the dopant species in the host tungsten oxide film is Re. The measurements were performed in two-terminal mode while passing a fixed current equal to 100 nA (nano Ampere) between the electrodes. Different indicated ppm levels of NO and $NO_2$ gas were applied successively to the gas sensor. The gas sensing layer for this embodiment of the gas sensor was deposited via reactive sputtering performed in the following conditions: the Ar:O pressure was maintained at 13 mTorr, and the Ar:O gas was made to flow at the rate of 20:13 sccm (standard cubic centimeter per minute). The gas sensing layer was deposited by co-sputtering of oxygen deficient tungsten oxide and Re targets using RF power of 240 Watt and 12 Watt respectively. The gas sensing layer was deposited at an average rate of about 0.14 Å/s (Angstrom per second) to ultimately have a thickness of about 1500 Å. The gas sensor was maintained at temperature of about 400° C. when the measurements were performed. In this case, the response due to the presence of the first species and second species of analyte ($NO_2$ and NO respectively) induces a response (change in resistance) ratio that is, on the average, very nearly 1.7. A response time that is "fast" and a recovery time that is "fast" are demonstrated. Furthermore, the baseline resistance is stable over time, and the response profile is "flat" when the level of analyte is maintained constant.

It has been estimated that the delay time associated with the response of the gas sensor as the flow of analyte is introduced/ withdrawn is expected to be of the order of few $10^1$ s. For example, referring to FIG. 7, we estimate the delay time to be less than 30 s.

Figure 8:
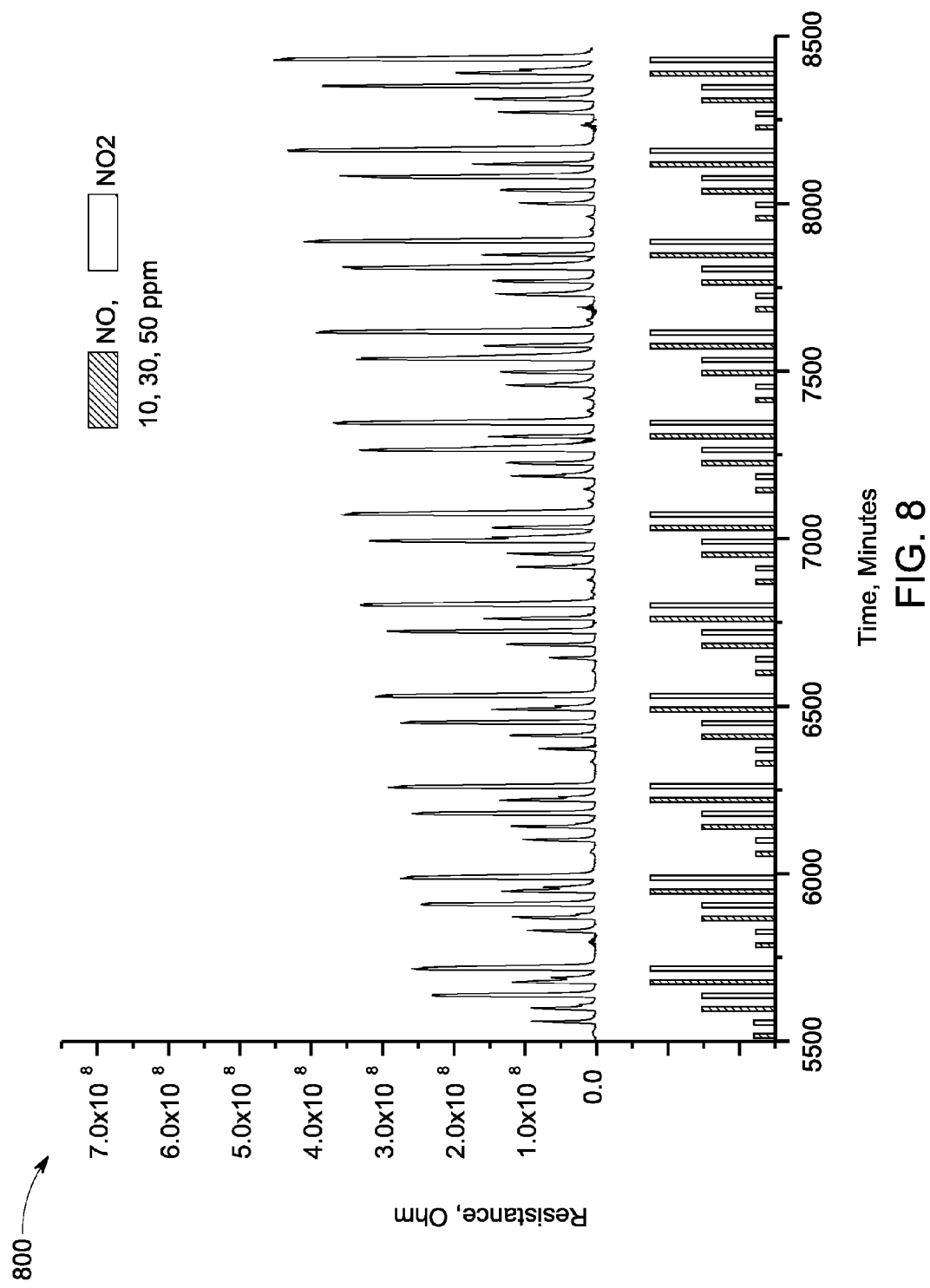
FIG. 8 is a graphical representation of the variation in gas sensor response upon exposure to different indicated NO and $NO_2$ gas levels, wherein the dopant species in a gas sensing layer of the gas sensor are Re and Ni, in accordance with one exemplary embodiment of the invention.

FIG. 8 is a graph 800 illustrating the resistance response of the gas sensor over time according to an exemplary embodiment of the invention when the dopant species in the host tungsten oxide film are Re and Ni. The measurements were performed in two-terminal mode while passing a fixed current equal to 250 nA between the electrodes. Different indicated ppm levels of NO and $NO_2$ gas were applied successively to the gas sensor. The gas sensing layer for this embodiment of the gas sensor was deposited via reactive sputtering performed in the following conditions: the Ar:O pressure was maintained at 4.9 mTorr, and the Ar:O gas was made to flow at the rate of 21.2:4.0 sccm (standard cubic centimeter per minute). The gas sensing layer was deposited by co-sputtering of W and Re targets using RF power of 280 Watt and 14 Watt respectively. The gas sensing layer was deposited at an average rate of about 0.75 Å/s (Angstrom per second) to ultimately have a thickness of about 1200 Å. The gas sensor was maintained at temperature of about 400° C. when the measurements were performed. The sample was tested continuously for a period of over 8500 min. Representative data obtained over the time period from about 550 min to about 8500 min is presented. In this case, the response due to the presence of the first species and second species of analyte ($NO_2$ and NO respectively) induces a response (change in resistance) ratio that is, on the average, very nearly 2. A response time that is "medium" and a recovery time that is "medium" are demonstrated. The highly reproducible response of the gas sensor when exposed to indicated levels of $NO_x$ over time, and the highly stable baseline resistance, demonstrate the excellent working life-time of the gas sensor.

Figure 9:
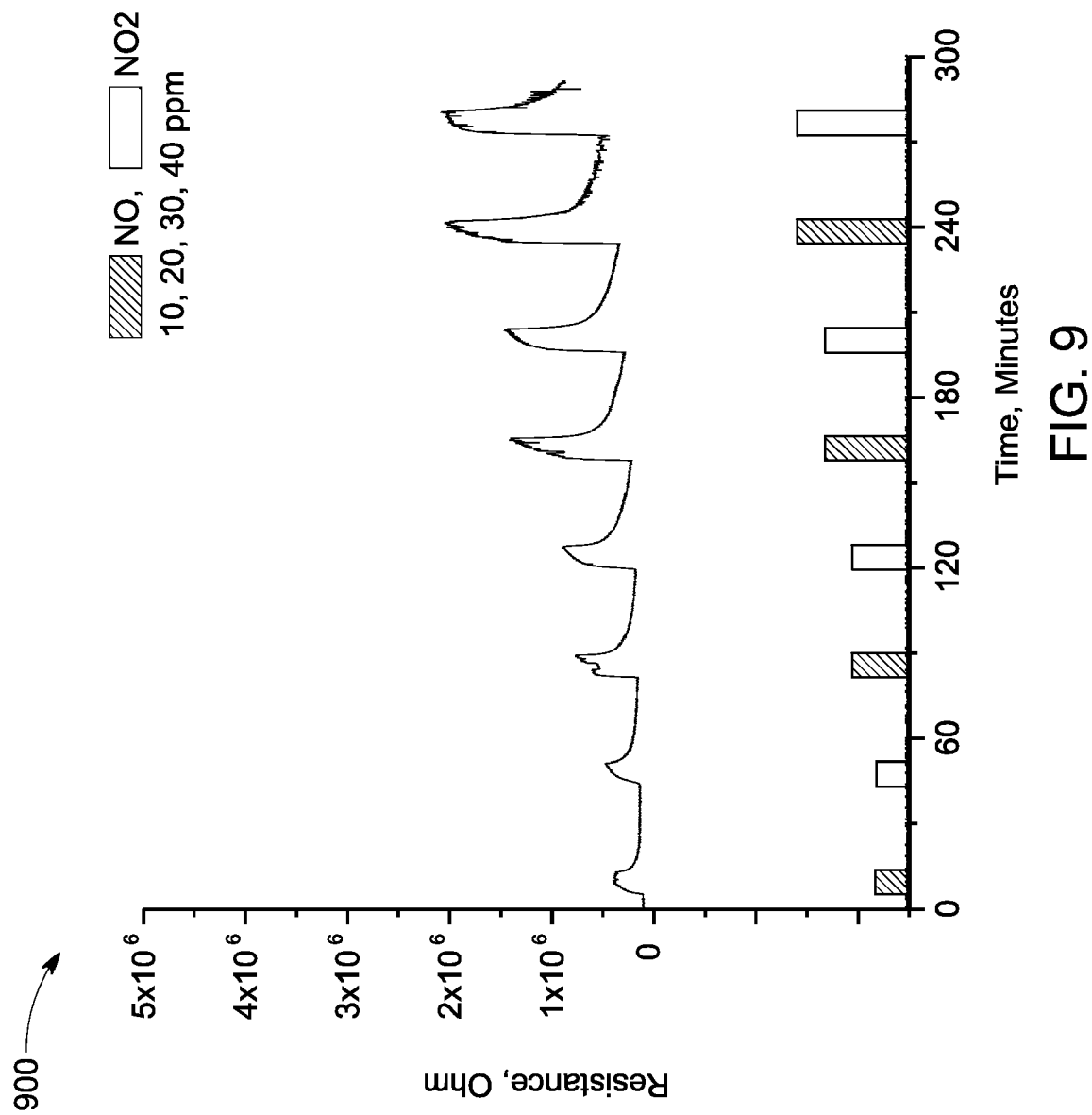
FIG. 9 is a graphical representation of the variation in gas sensor response upon exposure to different indicated NO and $NO_2$ gas levels, wherein the dopant species in a gas sensing layer of the gas sensor is Cr, in accordance with one exemplary embodiment of the invention.

FIG. 9 is a graph 900 illustrating the resistance response of the gas sensor over time according to an exemplary embodiment of the invention when the dopant species in the host tungsten oxide film is Cr. The measurements were performed in two-terminal mode while passing a fixed current equal to 250 nA between the electrodes. Different indicated ppm levels of NO and $NO_2$ gas were applied successively to the gas sensor. The gas sensing layer for this embodiment of the gas sensor was deposited via sputtering performed in the following conditions: the Ar:O pressure was maintained at 2.9 mTorr, and the Ar gas was made to flow at the rate of 15.4 sccm (standard cubic centimeter per minute). The gas sensing layer was deposited by co-sputtering of oxygen deficient tungsten oxide and Cr targets using RF power of 240 Watt and 12 Watt respectively. The gas sensing layer was deposited at an average rate of about 1.9 Å/s (Angstrom per second) to ultimately have a thickness of about 750 Å. The gas sensor was maintained at temperature of about 400° C. when the measurements were performed. In this case, the response due to the presence of the first species and second species of analyte ($NO_2$ and NO respectively) induces a response (change in resistance) ratio that is, on the average, very nearly unity.

In one embodiment, the gas sensor may be used to monitor and/or measure the concentration of at least one analyte in the exhausts of an automobile. For instance, the gas sensor may be positioned for enhanced monitoring and/or measurement of analytes within the exhaust system of an automobile. In another embodiment, a plurality of gas sensors may be positioned at different locations within the exhaust system of the automobile to monitor and measure the concentration of analytes in the exhausts. In another embodiment, a plurality of gas sensors may be positioned at different locations within the exhaust stream of the automobile. In another embodiment, the gas sensor may be used to monitor and/or measure the concentration of at least one analyte at other locations within the automobile. For instance, the gas sensor may be positioned for enhanced monitoring and/or measurement of analytes within the cabin of an automobile. In another embodiment, a plurality of gas sensors may be positioned at different locations within the automobile to monitor and measure the concentration of analytes within the cabin of the automobile.

Embodiments of the gas sensor of the present invention may also be used to monitor emission of $NO_x$ in applications including, but not limited to, aluminum, cement, fertilizer, glass, mineral wool, power, steel, sulphuric acid, and waste incineration industries. In the automobile sector, the gas sensor of the present invention may be used to monitor emissions in a variety of applications including, but not limited to, the emission of $NO_x$ from petrol, gasoline and diesel engine automobiles including, but not limited to, passenger cars, light commercial vehicles, lorries, trucks, and buses.

The gas sensor may also be used to meet the U.S. Environmental Protection Agency continuous emissions monitoring standards (CEMS) outlined in 40 C.F.R. §60 and 40 C.F.R. §75. The gas sensor may further be used to meet the European Union CEN emissions limit values. Still further, the gas sensors may be used in a continuous emissions monitoring system to determine "cap and trade" allowances as described by local and federal regulating authorities.

In another aspect, a gas sensor is arranged within an encapsulation in a flip-chip arrangement. In a flip-chip arrangement, the gas sensor is flipped upside down, such that all of the top sensitive surface area of the device including the area surrounding the sensitive areas of the device, are protected from gases to be monitored. An additional protective board protects the back surface of the chip. Directly over the sensitive area of the device, a slit, or opening in the ceramic board to which the chip's top surface is mounted, is created to allow the gases to flow to the gas sensing layer. A layer of high temperature stable conductive material, such as Pt or Au, may be used to interconnect the components of the gas sensor to leads in the encapsulation layer. This flip chip arrangement enables interconnect in a higher vibration and higher temperature, for example greater than 500° C., environments than conventional wire bonds, which are susceptible to fatigue failure. The interconnection using platinum and/or gold "bumps" to connect the components, such as the at least one the electrodes to the leads helps to enable the use of the gas sensor in harsh environments.

In one embodiment the gas sensor may be configured to be operable in harsh environments in which are present locations where the temperature is between about 200° C. and about 800° C. In another embodiment, the gas sensor may be configured to be operable in harsh environments in which are present locations with temperature is between about 200° C. and about 600° C. In yet another embodiment, the gas sensor may be configured to be operable in harsh environments in which are present locations with temperature is between about 300° C. and about 500° C.

The gas sensor is cost effective in that it has a long working life ($\sim 10^3$ hours) and provides highly repeatable readout. The cost effectiveness is further enhanced because of the simple modular design of these gas sensors allowing ready scaling of the manufacturing process to large volumes.

The gas sensor may be encapsulated in a packaging. The encapsulation further protects the gas sensor from the high temperature and corrosive atmosphere in the harsh environments where these gas sensors are likely to be used. The encapsulation acts to cover exposed surfaces of such elements of the device as the titanium layer, the electrodes, the first glass layer, the thermometer, the second glass layer, the heater, and the substrate, which do not by themselves, sense the gases. This encapsulation may also involve forming a bond with the underlying layer (substrate), so as to not permit flow of gases and corrosive materials (e.g., particulate matter, hydrocarbons) that would be detriment to the device over time. Examples of such suitable materials for encapsulation include, but are not limited to, silicon carbide, ceramic based epoxies such as those containing alumina, glass, quartz, silicon nitride, silicon dioxide and a combination thereof.

The encapsulation layer can be deposited by any known method, such as plasma enhanced chemical vapor deposition (PECVD), low pressure chemical vapor deposition (LPCVD), and a combination thereof. The encapsulation is such that at least a portion of the gas sensing layer remains exposed to ambient gases. With the application of an encapsulation the gas sensors may be protected in harsh environments and have a longer working life. Such protection against harsh environments would allow for the use of these sensors in a wide variety on settings, including but not limited to, boiling water reactor, automotive and locomotive petrol or diesel engine exhaust, industrial process (glass, aluminum, steel, and petroleum) plant exhaust. It would further protect the gas sensor from the particulate matter that may be present in the exhaust streams of the previously mentioned environments. Such particulate matter may potentially be detriment to the gas sensor as they may adhere to and/or corrode the gas sensor thereby hindering the detection of exhaust gases by hindering contact between the exhaust gases and the gas sensor.

While the invention has been described in detail in connection with only a limited number of embodiments, it should be readily understood that the invention is not limited to such disclosed embodiments. Rather, the invention can be modified to incorporate any number of variations, alterations, sub-

What is claimed as new and desired to be protected by Letters Patent of the United States is:

1. A gas sensor, comprising:
   a gas sensing layer comprising $WO_{3-\delta}$, wherein $0.35 \geq \delta > 0$, and comprising a dopant selected from the group consisting of Re, Ni, Cr, V, W, and a combination thereof; and
   at least one electrode positioned adjacent to layer of titanium and a response modification layer of a material selected from the group consisting of Ti, Ni, Cr, V, W, Re and a combination thereof, the at least one electrode being in communication with the gas sensing layer;
   wherein the gas sensing layer is capable of detecting at least one gas selected from the group consisting of NO, $NO_2$, $SO_x$, $O_2$, $H_2O$ and $NH_3$.

2. The gas sensor of claim 1, comprising:
   a substrate layer;
   a heating layer adjacent to the substrate layer;
   a first glass layer adjacent to the heating layer;
   a temperature sensing layer adjacent to the first glass layer;
   a second glass layer between the temperature sensing layer and the titanium layer.

3. The gas sensor of claim 1, wherein the gas sensing layer is configured for equisensitive response to two given gases.

4. The gas sensor of claim 1, wherein the gas sensing layer is configured to be operable in harsh environments.

5. The gas sensor of claim 1, wherein an analyte species filter material is disposed adjacent to the gas sensing surface of the gas sensing layer.

6. The gas sensor of claim 1, wherein the at least one electrode is composed of a material selected from the group consisting of Pt, Au, Ag, Ni, Ti, In, Sn, Cr, nickel oxide, titanium nitride, aluminum doped zinc oxide, indium tin oxide, and a combination thereof.

7. The gas sensor of claim 1, wherein the at least one electrode is composed of a multilayer stack of materials selected from the group consisting of Pt, Ti, Al, Au, Ag, Ni, Cr, In, titanium nitride, nickel oxide, aluminum doped zinc oxide, indium tin oxide, chrome, and a combination thereof.

8. The gas sensor of claim 1, wherein the at least one electrode is placed in a sandwich geometry, a side-by-side geometry, or combinations thereof.

9. The gas sensor of claim 1, wherein the gas sensing layer has a response time from about 1 s to about 100 s upon exposure to analyte.

10. The gas sensor of claim 1, wherein the gas sensing layer has a recovery time from about 1 s to about 100 s after exposure to analyte is withdrawn.

11. The gas sensor of claim 1, wherein said at least one electrode comprises at least two electrodes and an electrical resistance between said at least two electrodes is less than about $100000\Omega$.

12. The gas sensor of claim 1, wherein the at least one electrode can be placed in an interdigitated geometry, an inline geometry, or combinations thereof.

13. The gas sensor of claim 1, wherein the gas sensor is arranged in a flip-chip arrangement.

14. The gas sensor of claim 1, wherein the gas sensing layer is configured for detection of analyte levels from about 1 ppm to about 1000 ppm.

15. The gas sensor of claim 1, wherein the gas sensor is configured to be operable as a resistor, a field effect transistor, a capacitor, a diode, and a combination thereof.

16. The gas sensor of claim 1, wherein the gas sensor is configured so that its response may be monitored via resistive measurements, potentiometric measurements, or combinations thereof.

17. The gas sensor of claim 1, wherein the electrode thickness is from about thickness 500 Å to about 10000 Å.

18. The gas sensor of claim 1 when the at least one electrode comprises a multilayer stack of materials, wherein a thickness of each layer of the multilayer stack is from about 100 Å to about 2000 Å.

19. The gas sensor of claim 1, wherein the response modification layer thickness is from about 10 Å to about 100 Å.

20. The gas sensor of claim 1, wherein the titanium layer thickness is from about 5 Å to about 100 Å.

21. The gas sensor of claim 1, wherein the gas sensing layer thickness is from about 300 Å to about 5000 Å.

22. The gas sensor of claim 1, wherein the concentration of the dopant in the gas sensing layer can be from about 0.2 mol % to about 5 mol %.

23. The gas sensor of claim 1, wherein the response of the gas sensor may be measured using an AC detection technique, a DC detection technique, or a combination thereof.

24. A gas sensor array, wherein a plurality of gas sensors of claim 1 are placed adjacent to each other.

25. An automobile having a system for gas sensing, comprising:
   an exhaust system to transport gases; and
   a gas sensor, comprising:
   a gas sensing layer comprising $WO_{3-\delta}$, wherein $0.35 \geq \delta > 0$, and comprising a dopant selected from the group consisting of Re, Ni, Cr, V, W, and a combination thereof;
   at least one electrode positioned within a layer of titanium and a response modification layer comprising a material selected from the group consisting of Ti, Ni, Cr, V, W, Re and a combination thereof, the at least one electrode being in communication with the gas sensing layer, and
   wherein the gas sensing layer is capable of detecting at least one gas selected from the group consisting of NO, $NO_2$, $SO_x$, $O_2$, $H_2O$, and $NH_3$.

* * * * *

UNITED STATES PATENT AND TRADEMARK OFFICE
CERTIFICATE OF CORRECTION

PATENT NO.         : 7,827,852 B2
APPLICATION NO.    : 11/961092
DATED              : November 9, 2010
INVENTOR(S)        : Cui et al.

Page 1 of 1

It is certified that error appears in the above-identified patent and that said Letters Patent is hereby corrected as shown below:

In Column 9, Line 63, delete "but a" and insert -- but --, therefor.

In Column 10, Line 10, delete "$NO_1$" and insert -- $NO_x$ --, therefor.

In Column 14, Line 52, delete "on" and insert -- of --, therefor.

Signed and Sealed this
Fourteenth Day of June, 2011

David J. Kappos
*Director of the United States Patent and Trademark Office*